United States Patent

Cueman et al.

[11] Patent Number: 5,823,978
[45] Date of Patent: Oct. 20, 1998

[54] LOW MODULUS SYNTHETIC FIBER CASTING SYSTEM

[75] Inventors: Glenn F. Cueman; Henry L. Richbourg, Jr., both of Davidson; Tony A. Williamson, Troutman, all of N.C.

[73] Assignee: Clinitex Medical Corporation, Huntersville, N.C.

[21] Appl. No.: 639,271

[22] Filed: Apr. 24, 1996

[51] Int. Cl.$^6$ ............................................. A61F 5/00
[52] U.S. Cl. ............................ 602/6; 602/8; 602/44
[58] Field of Search ......................... 602/1, 6, 8, 44, 602/45, 75–77, 900

[56] References Cited

U.S. PATENT DOCUMENTS

| | | | |
|---|---|---|---|
| 2,964,174 | 12/1960 | Litchfield | 206/59 |
| 3,062,370 | 11/1962 | Morin | 206/63.2 |
| 3,152,692 | 10/1964 | Johnston | 206/59 |
| 3,630,194 | 12/1971 | Boardman | 128/90 |
| 4,020,832 | 5/1977 | Kirkpatrick | 128/90 |
| 4,131,114 | 12/1978 | Kirkpatrick | 128/90 |
| 4,153,052 | 5/1979 | Tsuk | 128/90 |
| 4,344,423 | 8/1982 | Evans | 128/90 |
| 4,376,438 | 3/1983 | Straube | 128/90 |
| 4,411,262 | 10/1983 | von Bonin | 128/90 |
| 4,433,680 | 2/1984 | Yoon | 128/90 |
| 4,498,467 | 2/1985 | Kirkpatrick | 128/90 |
| 4,502,479 | 3/1985 | Garwood et al. | 128/90 |
| 4,609,578 | 9/1986 | Reed | 428/76 |
| 4,667,661 | 5/1987 | Scholz | 128/90 |
| 4,774,937 | 10/1988 | Scholz | 128/90 |
| 4,800,872 | 1/1989 | Buese et al. | 128/90 |
| 4,898,159 | 2/1990 | Buese | 128/90 |
| 4,960,116 | 10/1990 | Milner | 128/90 |
| 5,027,803 | 7/1991 | Scholz | 128/89 |
| 5,052,380 | 10/1991 | Polta | 128/90 |
| 5,061,555 | 10/1991 | Edenbaum | 428/253 |
| 5,088,484 | 2/1992 | Freeman et al. | 602/44 |
| 5,250,344 | 10/1993 | Williamson | 428/143 |
| 5,342,291 | 8/1994 | Scholz et al. | 602/41 |
| 5,354,259 | 10/1994 | Scholz | 602/8 |
| 5,403,267 | 4/1995 | Pearce | 602/8 |
| 5,405,643 | 4/1995 | Scholz | 427/2.31 |
| 5,423,735 | 6/1995 | Callinan | 602/8 |
| 5,449,550 | 9/1995 | Yasis | 428/254 |
| 5,461,885 | 10/1995 | Yokoyama et al. | 602/8 |
| 5,474,522 | 12/1995 | Scholz | 602/8 |
| 5,476,440 | 12/1995 | Edenbaum | 602/8 |
| 5,505,692 | 4/1996 | Cho | 602/8 |
| 5,540,982 | 7/1996 | Scholz et al. | 602/8 |

OTHER PUBLICATIONS

Norma Hollen & Jane Saddler, Textiles, Chapters 9 (Fiber Blends) and 10 (Conventional Yarn Spinning), pp. 85–101, 1968.

*Primary Examiner*—Wynn Wood Coggins
*Assistant Examiner*—Jennifer R. Sadula
*Attorney, Agent, or Firm*—Dougherty & Dremann

[57] ABSTRACT

An orthopedic casting material having strength and porosity characteristics which heretofore have been associated only with high modulus fibers, while using casting material comprising a fabric made from a multi-filament, low modulus fiber. The fabric is impregnated with a reactive resin which hardens by wetting with a curing agent. A method for making an orthopedic cast and the resulting cast product are also disclosed, as is coloring of the cast product in a variety of desired colors and patterns.

78 Claims, 11 Drawing Sheets

LOW MODULUS SYNTHETIC FIBER CASTING SYSTEM

FIELD OF THE INVENTION

The present invention relates to the application of orthopedic casts, and particularly to the application of orthopedic casts formed from low modulus, multi-filament fibers, and a moisture-curing plastic material.

BACKGROUND OF THE INVENTION

Orthopedic casts are used for the treatment of bone fractures or other conditions requiring immobilization of a body member. These casts are generally formed from a strip of fabric or "scrim" material coated with a substance which hardens into a rigid structure after the strip has been wrapped around the body member.

One of the first hardening substances used for casts was plaster-of-Paris. Plaster-of-Paris casts, however, have a number of disadvantages including a low strength-to-weight ratio which results in a finished cast which is bulky and very heavy. A plaster-of-Paris cast will break down in water, thus making bathing or showering difficult. Additionally, plaster-of-Paris casts are not air-permeable and do not allow for evaporation of moisture from the skin beneath the cast. This non-breatheability may lead to skin irritation or infection. After the application of a plaster-of-Paris cast, the wearer must wait for hours until the cast hardens. Typically this can require a wearer to wait from 24 to 72 hours before weight can be applied to the cast. These drawbacks have stimulated the search for other hardening substances having improved properties over plaster-of-Paris.

Synthetic, polymer-reinforced materials were proposed as potential replacements for plaster-of-Paris in orthopedic casts. Synthetic, polymeric casts are generally much lighter than plaster-of-Paris, impervious to water and provide excellent X-ray clarity. Initially, they did not gain broad acceptance among physicians and cast technicians due to their failure to meet certain performance requirements.

A good synthetic casting material must be safe to apply and non-irritating to the skin of the wearer. Thus, resins which give off toxic volatile compounds or which expose the body to unsafe heat levels during application are unacceptable. A suitable resin must allow sufficient "working time" e.g., 2 to 3 minutes, in which the wrapping is accomplished and the cast is pressed into shape. After the cast is shaped, the resin should harden rapidly, e.g., in 5–15 minutes, into a rigid, high-strength, weight-bearing cast. In addition to the foregoing requirements, a good synthetic casting material should provide good lamination between the fabric layers of the cast, be porous enough to allow evaporation of moisture from the skin, have good X-ray clarity, low flammability and a shelf life of at least twelve months under room temperature storage conditions.

In the mid 1980s, a synthetic casting material was developed which had improved strength. This casting material became quite popular because it provided improved strength and rigidity within 15–30 minutes after application with a minimum of overlapping layers. These results were primarily achieved by modifying the scrim or tape material which is impregnated with the resin. As provided in Garwood, U.S. Pat. No. 4,502,479, the scrim material comprised a high strength and high modulus fabric made from a monofilament fiber having an initial modulus of elasticity greater than $8 \times 10^6$ pounds per square inch. The fabric was impregnated with a reactive resin which hardened by wetting with a second reactive chemical or catalyst solution (curing agent). After wetting, (e.g. by soaking for about 30 seconds) the material, when wrapped upon itself to form a cylindrical laminate of eight or less layers has a load-bearing strength sufficient for weight bearing (for a 2-inch diameter cylinder) 20 pounds per inch of cylinder length within 30 minutes after exposure to water.

The term "high modulus" as used in Garwood describes the fabric component of the casting material, specifically the degree of resistance to deformation or bending, and is expressed in terms of the modulus of elasticity. Modulus of elasticity is the ratio of change in stress to the change in strain which occurs when a fiber is mechanically loaded. According to Garwood, U.S. Pat. No. 4,502,479, the initial modulus of elasticity of the fiber should be greater than about $8 \times 10^6$ lbs/square inch. Such fibers include continuous filament E-fiberglass, polyaramid filament known as Kevlar® 49 (available from E.I. DuPont de Nemours and Company), ceramic fibers such as Nextel® (available from 3M Company) continuous filament graphite such as Thornel® (available from Union Carbide Corp.), boron fiber (such as made by Avco Corp.), and metal fibers such as stainless steel filaments which, when sufficiently fine can be formed into fabrics by weaving or knitting. These high modulus fibers impart a high degree of strength and rigidity to the cast. They may be combined with low to intermediate modulus materials when the flexibility of such yarns enables easier fabrication of the fabric. Low modulus fibers are those having an initial modulus of elasticity of less than about $3 \times 10^6$ lbs/in$^2$ and include cotton, polyester (such as "Dacron"), polypropylene, "Orlon" (DuPont), "Dynel"® (Union Carbide), "Nomex"™ (Dupont) and nylon. An example of a fiber with an intermediate modulus is polyvinyl alcohol fiber known as "Kuralon" (available from Kuraray Co., Ltd.). Although hybrid fabrics are useful in making orthopedic casts, a majority of high modulus fiber is necessary for adequate cast rigidity and strength.

The problem with the composition of materials taught by Garwood is that most high modulus fibers are very expensive, with the notable exception of fiberglass. However fiberglass imposes limits on how the underlying fabric can be prepared. While non-glass high modulus fibers are feasible in theory, in the real world they are economically undesirable. The only practical high modulus fiber which is both inexpensive and strong is fiberglass. When urethane resin is put on fiberglass, it forms a sheath around each fiber and stays on the outside of the fiber and causes to the fibers to adhere together. The combination of high strength fibers results in a strong, rigid shell.

It is possible to produce a fabric from fiberglass. However, fiberglass is difficult to work with. To knit a fiberglass tape requires special equipment. One can knit fiberglass tapes only in a certain way, which does not allow production of many desirable types and widths of fabrics. Fiberglass tape that was developed twelve years ago is very similar to the fiberglass tape being used today. Yet, in the field of orthopedic casts, this is state of the art. Today, more doctors use fiberglass cast tape and urethane resin than any other materials to produce casts. Today's knitted fiberglass tape is still coated with urethane to form the substrate for the cast. No urethane impregnates the fiberglass, as it resides solely as a coating on the outside of the glass.

DESCRIPTION OF THE PRIOR ART

Applicants are aware of the following U.S. patents concerning orthopedic casts formed of moisture-curing synthetic material.

| U.S. Pat. No. | Inventor | Issue Date | Title |
| --- | --- | --- | --- |
| 4,502,479 | Garwood et al. | 03-05-1985 | WATER-ACTIVATED CASTING MATERIAL |
| 5,354,259 | Scholz | 10-11-1994 | MICROFIBER FILLERS FOR ORTHOPEDIC CASTING TAPES |
| 5,403,267 | Pearce et al. | 04-04-1995 | ORTHOPEDIC BANDAGES WITH LOW MODULUS FILAMENTS |
| 5,474,522 | Scholz | 12-12-1995 | MICROFIBER FILLERS FOR ORTHOPEDIC CASTING TAPES |

Garwood teaches an orthopedic casting material having improved strength by using high modulus fibers. However in the Scholz patents '259 and '522 many reasons are identified why high modulus fibers such as fiberglass are not advantageous. In order to improve strength of a low modulus substrate, Scholz adds microfibers to the prepolymer. Pearce claims to achieve sufficient rigidity even when adding in elastic fibers.

SUMMARY OF THE INVENTION

The present invention is an optimized low modulus fiber which is reacted with a resinous material to produce a cast, the strength of the resulting cast being equal to or greater than a cast made from fabric containing a high modulus fiber.

The advantage of the invented process is that low modulus fibers can be processed and handled in far more ways than fiberglass or other high modulus fibers. Any fabrics from nonwovens to wide or narrow strips of material can be produced.

It was determined that a low strength fiber could be developed that has physical properties which allow urethane to react within it, and be absorbed into it. As the resin hardens, the strength in the resulting construction is equivalent of a cast produced with high strength fibers such as fiberglass.

Low modulus fiber based products have been tested in the past and none have proved to be a suitable substitute for fiberglass. Starting with a filament of a yarn, a regular, low strength, synthetic filament (well under the $3 \times 10^6$ modulus of elasticity) was combined into a multi-filament yarn. This yarn was then used to form a knitted fabric. The yarn was optimized to be the same diameter as a single strand of fiberglass, but each yarn is made up of between one hundred (100) and five hundred (500) individual filaments. Each individual filament provides surface area on which the resinous polymer can be deposited. Actual surface area of the combined fibers is many times greater than a single strand of fiberglass. The interstices between the individual filaments provide further repositories for the resin. Depending on the fiber selection, urethane can also be absorbed into the surface of the fiber itself providing a truly integrated structure. More resin can be applied to this fabric with less resin actually residing on the exterior surface of the yarn.

The invention provides is a fabric that is more conformable, and has a smoother texture than fiberglass. This optimized fiber can be knit into a wide fabric (greater than 3 inches or 7.6 centimeters), and slit to the desired width. This process is much less expensive than knitting materials to the desired width. Another advantage of this system is that the fabric can be made as a nonwoven, using a process very similar to the process used in the production of paper. The result of this system is the creation of a cast tape system that is just as strong as, if not stronger than, fiberglass.

OBJECTS OF THE INVENTION

The principal object of the present invention is to provide an optimized composition of matter which can be used to produce orthopedic casts for use in the treatment of bone fractures and which has good strength.

A further object of this invention is to provide a method of selecting fibers, which are not high modulus, to produce a cast that is as strong as a cast made from materials including high modulus fibers.

Another object of the invention is to provides an optimized composition of matter that uses low modulus fibers to produce nonwoven fabrics, woven fabrics, knitted fabrics capable of being produced in a variety of widths or of being cut to the desired width.

Another object of the invention is to provide a orthopedic cast system that eliminates the use of fiberglass.

Another object of the invention is to provide an optimized composition of matter that can be used cost effectively to produce orthopedic casts.

Another object of the invention is to provide an orthopedic cast system which has improved radiolucency over fiberglass casting systems.

A further object of the invention is to provide a means of producing a cast which can be colored without having to place any dye in the prepolymer.

BRIEF DESCRIPTION OF THE DRAWINGS

The foregoing and other objects will become more readily apparent by referring to the following detailed description and the appended drawings in which.

DETAILED DESCRIPTION

Figure 1:
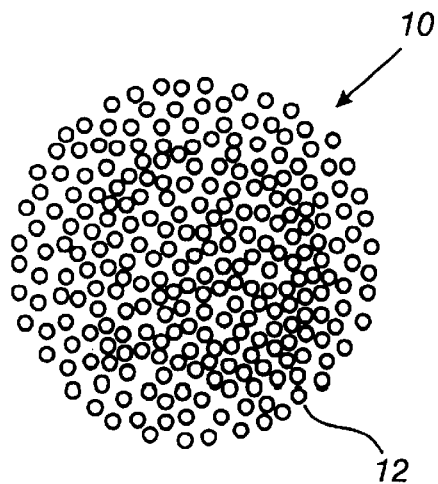
FIG. 1 is an enlarged cross sectional view of a multi-filament fiber yarn.

Referring now to the drawings, and particularly to FIG. 1, the invented multi-filament yarn 10 is made up of between 100 and 500 individual filaments 12. Each filament ranges from 6 denier to 0.5 denier with the optimal range being 3 denier to 0.8 denier. In most cases each filament within the yarn will be the same denier. The yarn made from these filaments has a yarn count ranging from 7 to 36 with a preferred range of 12 to 36. While a one ply yarn is acceptable, multiple ply yarns are preferred, particularly two ply yarns. Each of these multi-filament yarns has an initial modulus of elasticity of less than $3 \times 10^6$ pounds per square inch.

Figure 2:
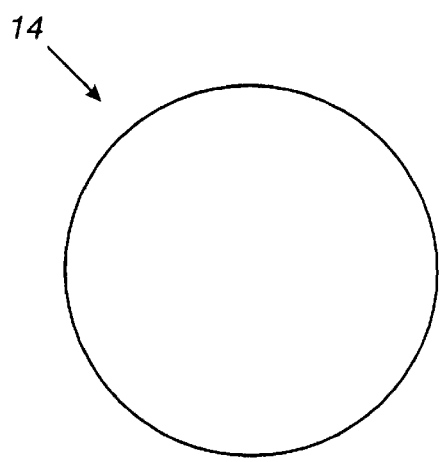
FIG. 2 is an enlarged cross sectional view of a single filament fiberglass yarn.
Figure 4:
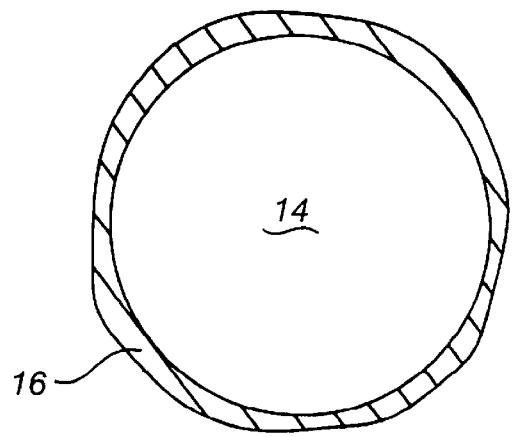
FIG. 4 is an enlarged cross sectional view of a single filament fiberglass yarn and urethane prepolymer.

By contrast the typical fiberglass fabric is made from monofilament fiberglass fibers 14, FIG. 2, having an initial modulus of elasticity of greater than $8 \times 10^6$ pounds per square inch. Fiberglass is also available in multi-filament yarns, though many of these have twenty or fewer filaments per strand. While they provide a greater surface area, it is still less than that of low modulus yarns which have in excess of one hundred filaments per yarn 10. When reactive fluid polyisocyanate prepolymer resin is applied to the fiberglass fiber, the resin 16, FIG. 4, sits on the surface of the fiber 14. Only a small amount of resin can be applied to these fibers before the resin will start to drip off.

Figure 3:
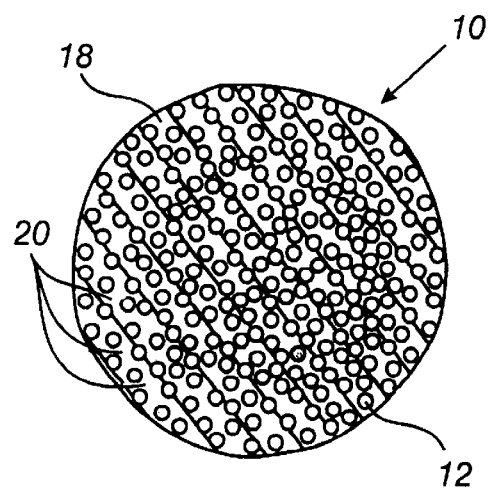
FIG. 3 is an enlarged cross sectional view of a multi-filament fiber yarn and the urethane prepolymer.

With low modulus multi-filament yarns 10, the reactive fluid polyisocyanate prepolymer resin 18 not only resides on the exterior of each filament 12, but also in the interstices 20, FIG. 3, between the individual filaments. This yarn construction results in the ability to accept a much greater range of prepolymer than can be accepted by yarns made from glass fibers. Because much of the prepolymer is held between the individual filaments of the yarn and in the interstices of the yarn, it is not necessary or even desirable to have as much prepolymer sitting on the exterior surface of the yarn as with conventional glass fibers. However, it should be noted that if desired, as much prepolymer may be put on the exterior of the yarn as would be on the exterior of a glass fiber, but this will result in a much greater percentage of prepolymer to fiber that in an ordinary fiberglass cast tape application.

Figure 5:
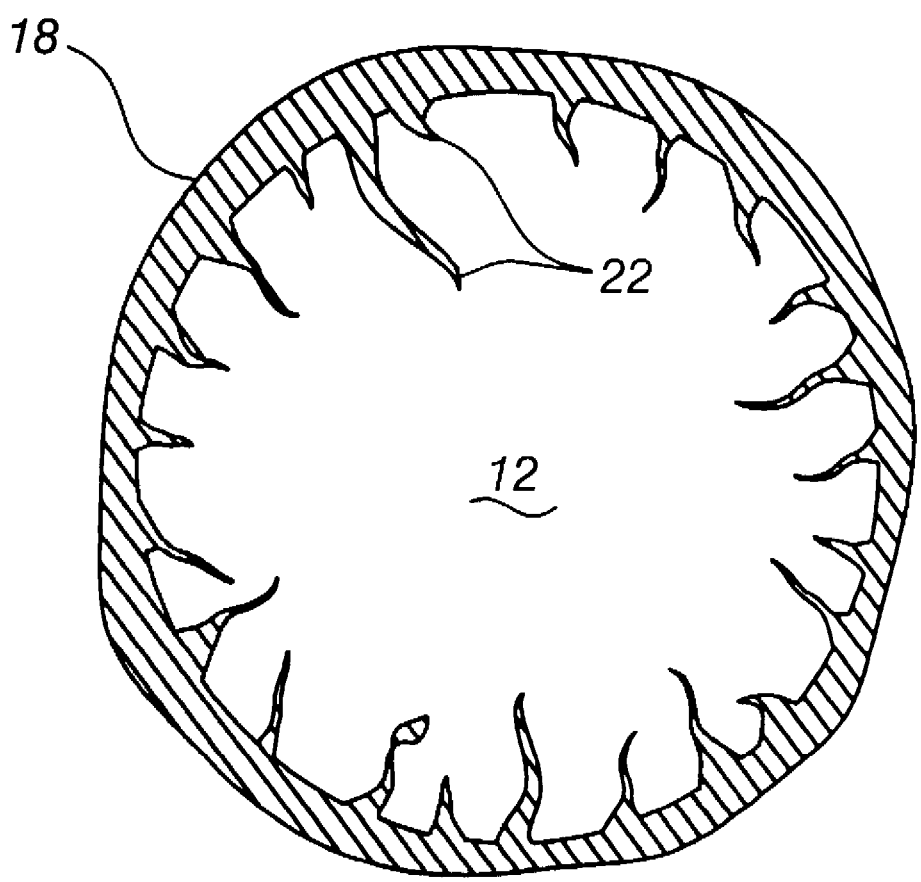
FIG. 5 is an enlarged cross sectional view of one embodiment of a single filament in the multi-filament fiber yarn.

In the optimization of the tape fabric, another important consideration is the selection of materials to be used for the individual filaments. From this standpoint, fibers which are porous and/or have a rough surface, FIG. 12, interact more favorably with the prepolymer than fibers which have a smooth surface, such as fiberglass, FIG. 13. With a rough surface, the prepolymer 18 spreads over the surface of the individual fiber, and penetrates any crevices, grooves or holes 22, FIG. 5, in the fiber. Then, after it is reacted, it gains mechanical strength through the interaction of the hardened polymer which may form sites for interaction with the ledges, and voids in the filaments, providing a mechanical attachment to the surface of the individual fibers.

The individual fibers or filaments can be either synthetic material or natural material. Examples of some of the synthetic fibers or filaments that can be used are: polyester, polypropylene, nylon, aramid, polyethylene, polytetrafluoroethylene, polyvinylchloride, polyvinylidinechloride, acrylic, polystyrene, polyethylene tetraphalate, polyurethane and mixtures thereof. Synthetic groups which are specifically useful are acrylics, polyolefins, celluloses and mixtures thereof. These groups yield fibers with the physical characteristics which are preferred in this application. It is also feasible to use natural fibers such as cotton, ramie, linen, hemp, silk and flax and mixtures thereof. It may also be advantageous to combine synthetic with natural fibers in the construction of the yarn or fabric.

Figure 14:
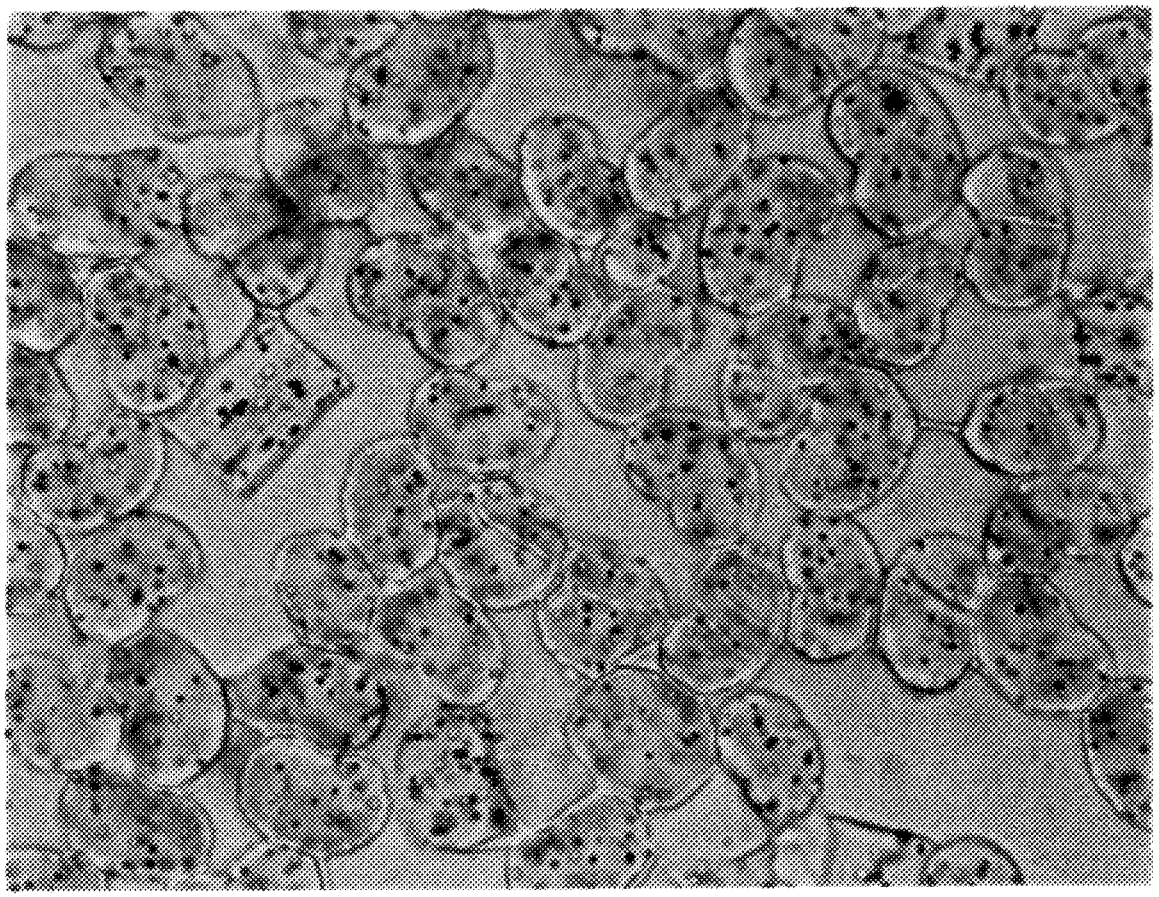
FIG. 14 is a photomicrograph of a cross section of several invented filaments at a magnification of 1000×.

The yarn 10 was optimized to be the same diameter as a single strand of fiberglass 14, but each yarn is made up of from one hundred (100) to five hundred (500) individual filaments 12. Each individual filament provides surface area on which the resinous polymer can be deposited, FIG. 14. Actual surface area of the combined fibers is many times greater than in a single strand of fiberglass. The interstices between the individual filaments provide further repositories for the resin. More resin can be applied to this fabric with less resin actually residing on the exterior surface of the yarn.

Figure 8:
FIG. 8 is a photomicrograph of the invented fabric at a magnification of 15×.
Figure 9:
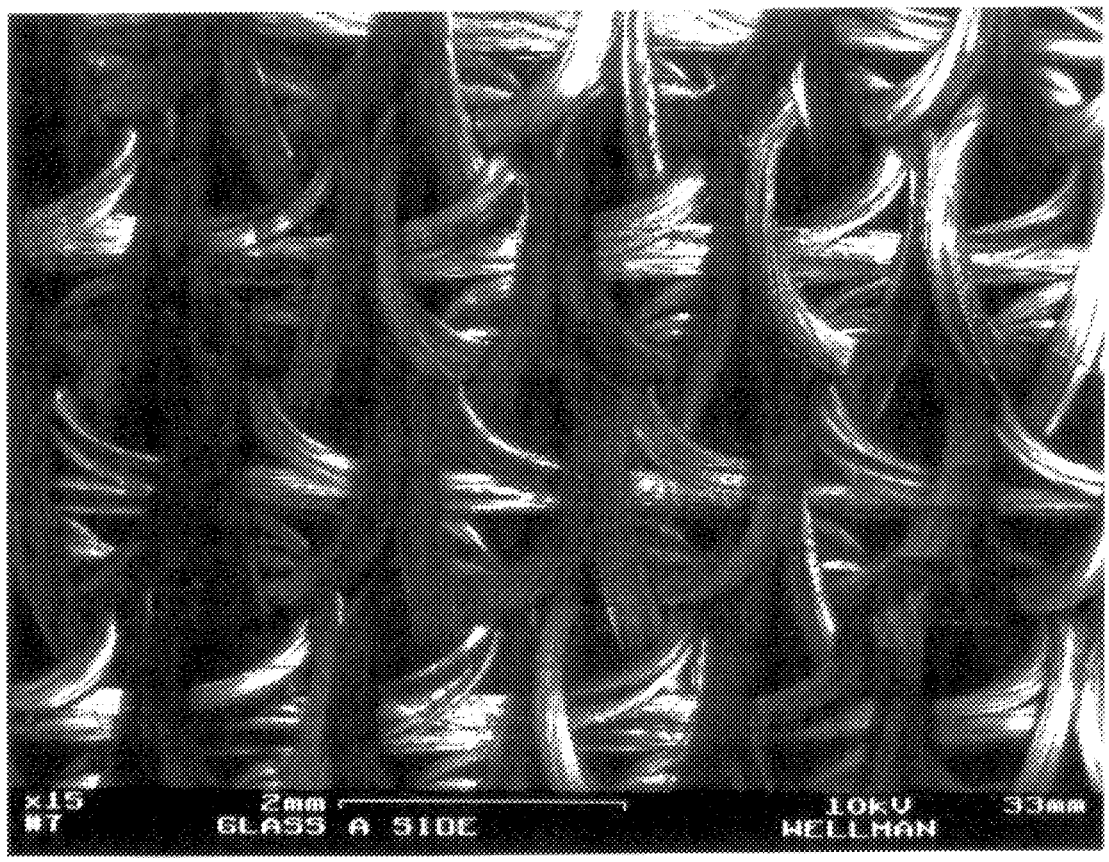
FIG. 9 is a photomicrograph of the current art fiberglass fabric at a magnification of 15×.
Figure 10:
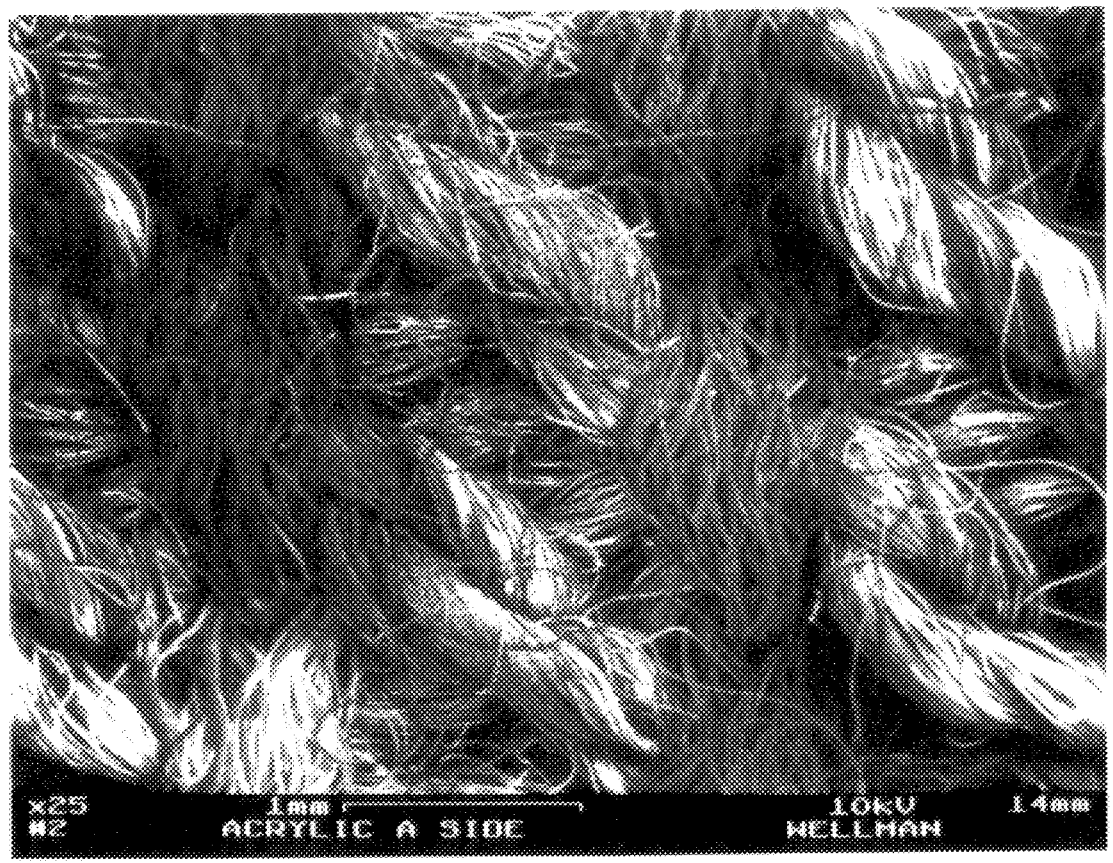
FIG. 10 is a photomicrograph of the invented fabric at a magnification of 25×.
Figure 11:
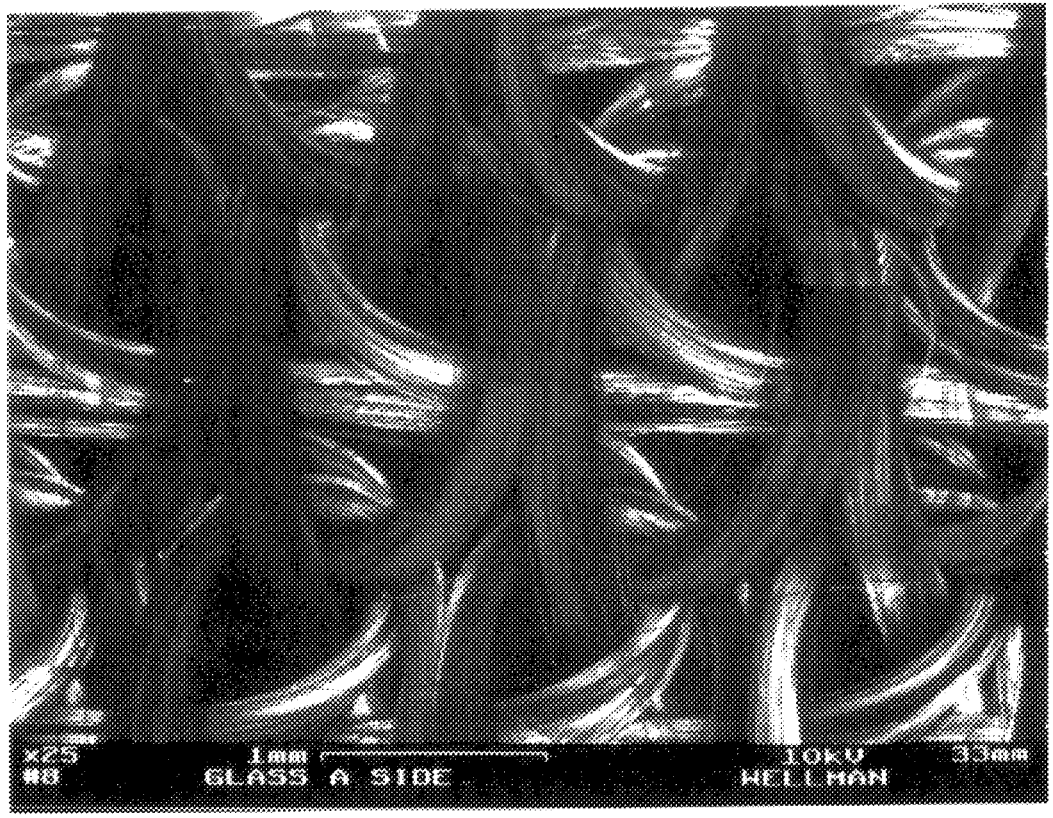
FIG. 11 is a photomicrograph of the current art fiberglass fabric at a magnification of 25×.

These yarns are then brought together to form a substrate. As discussed above, the yarns are typically comprised of low modulus fibers that include acrylics, polyolefins, celluloses, and mixtures thereof. The construction of the substrate should be sufficiently bulky, FIG. 8, to permit absorption of a curable polyurethane prepolymer that will produce a weight bearing cast. By comparison the fiberglass fabric, FIG. 9, does not have the same bulk. Compare the photomicrographs of FIGS. 10 and 11, both taken at 25×. FIG. 10 shows the bulk of the low modulus system, FIG. 11 shows fiberglass.

Figure 12:
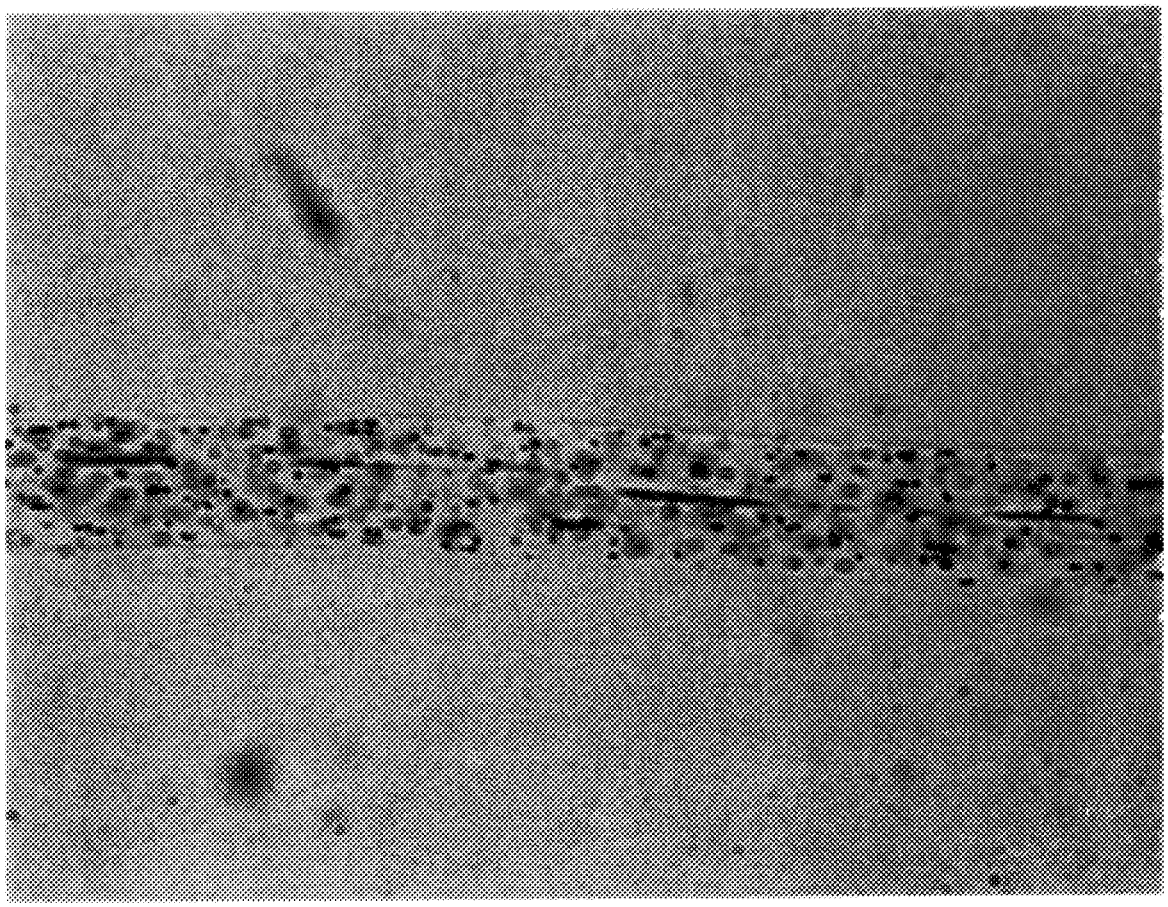
FIG. 12 is a photomicrograph of the invented filament at a magnification of 1000×.
Figure 13:
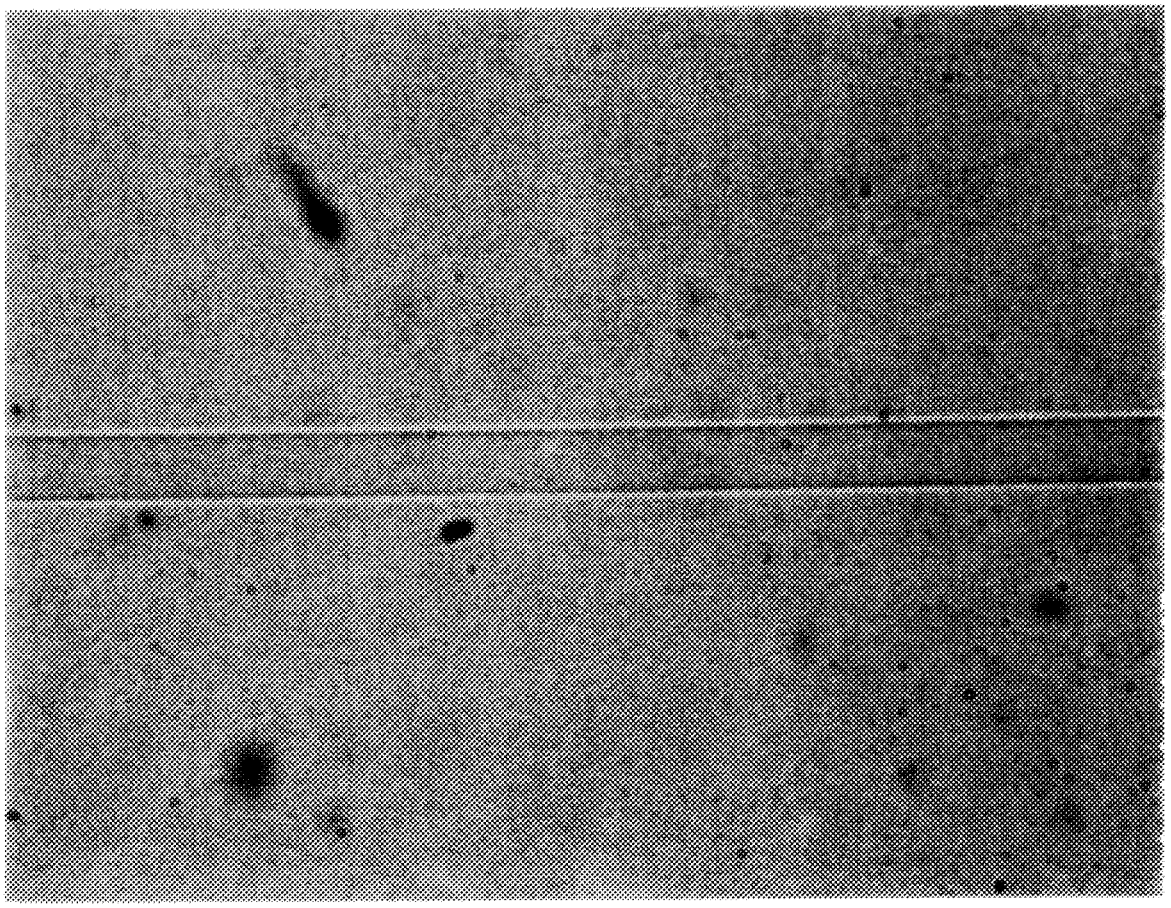
FIG. 13 is a photomicrograph of the current art fiberglass filament at a magnification of 1000×.

In a preferred embodiment, the substrate or fabric is made up of acrylic fibers, FIG. 12. However, these acrylic fibers can be blended with polyester, cotton, or any other low modulus fiber.

One element of the substrate's absorbency is the number of fibers per strand cross section of yarn, FIG. 1. As this increases so does its absorbency of the polyurethane prepolymer. The range of fibers per cross section of yarn is between 100 and 500. It is preferable to have a range of 150 to 400, though approximately 250 fibers per cross section has worked well in testing.

Figure 6:
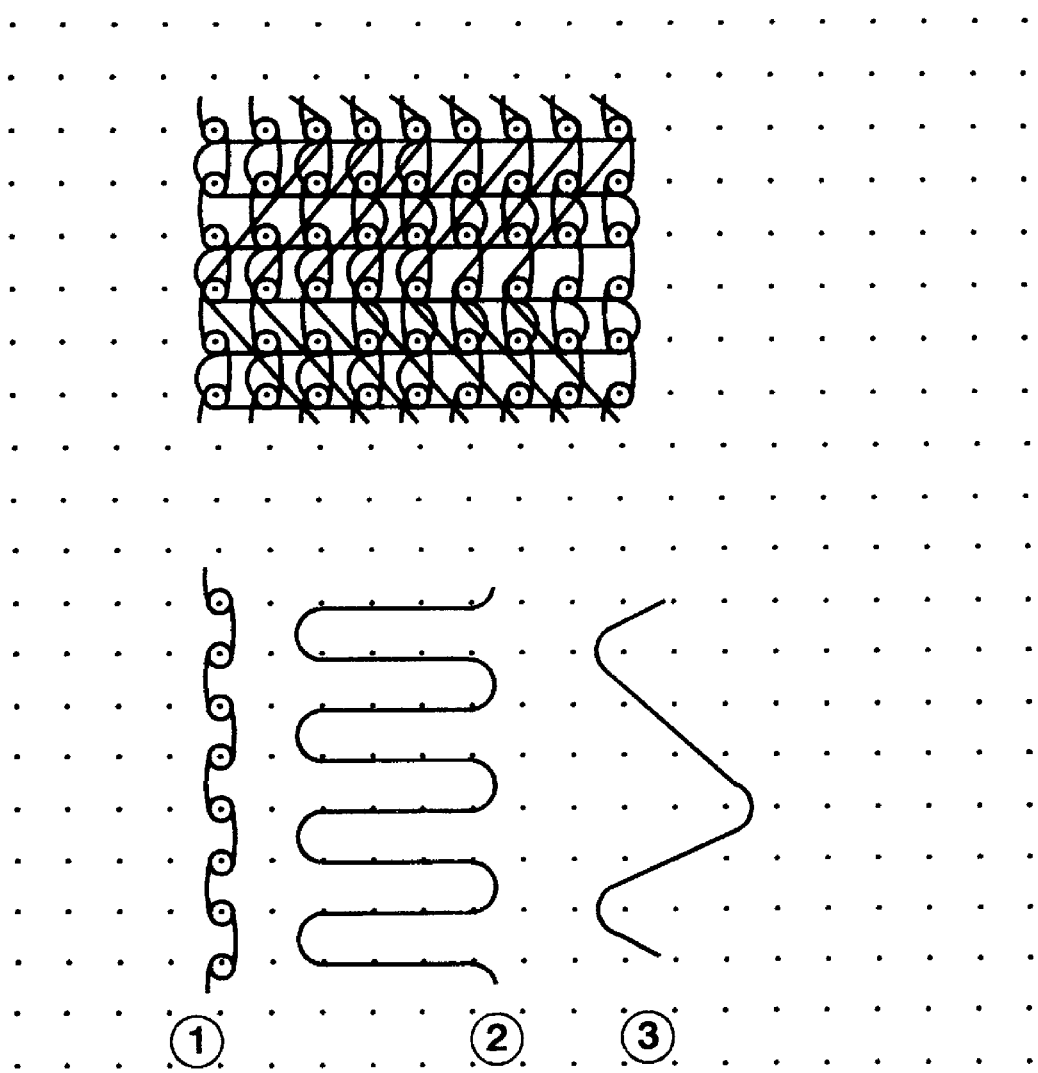
FIG. 6 is a three bar knit using the fibers of the present invention.
Figure 7:
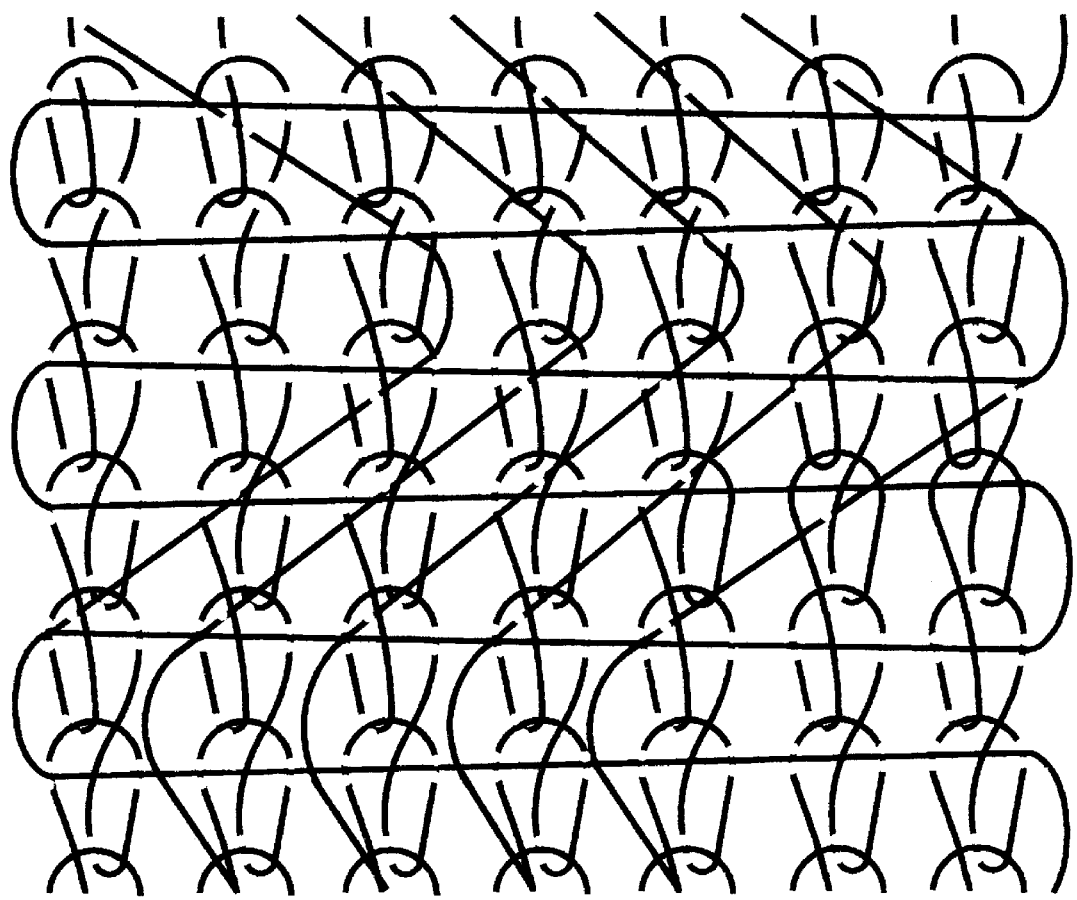
FIG. 7 is an enlarged front view of one embodiment of the knitted substrate obtainable with the present invention.

Another factor that can affect the absorbency of the polyurethane prepolymer is the construction of the substrate. Yarn 10 is used to form a fabric. The use of low modulus fibers to produce a fabric allows woven, non-woven or knitted constructions. This is not possible with a high modulus fiber like fiberglass which can only be knitted or woven in a limited number of ways to produce a tape with some give and the requisite porosity and stretch. What has been found to work particularly well in this application is a knitted fabric which is classified as a herringbone twill, FIGS. 6 and 7.

The resin is applied to the fabric as a polyisocyanate prepolymer formed by the reaction of an isocyanate and a polyol. It is preferred to use an isocyanate which has low volatility, such as diphenylmethane disocyanate (MDI) rather than a more volatile material such as toluene disocyanate (TDI). Suitable isocyanates include 2,4-toluene disocyanate, 2,6-toluene disocyanate, and mixtures of these isomers; 4,4'-diphenylmethane disocyanate, 2,4-diphenbylmethane disocyanate and mixtures of these isomers together with possible small quantities of 2,2-diphenylmethane disocyanate (typical of commercially available diphenylmethane disocyanate), and aromatic polyisocyanates and their mixtures such as those derived from phosgenetion of the condensation product of aniline and formaldehyde. Typical polyols for use in the prepolymer system include: polypropylene ether glycols (available from Dow under the tradename Voranol, and from Bayer under the tradename Multranol), polypropylene ether triols (available from Dow under the tradename Voranol and from Olin under the tradename Poly-G), polytetramethylene ether glycols (available from Union Carbide, BASF Wyandotte under the tradename Pluracol, and Quaker Oats Company under the tradename Polymeg), polycaprolactone diols (available from Union Carbide under the tradename Tone), polyester polyols (hydroxyl terminated polyesters obtained from the esterification of dicarboxylic acids and diols; available from Bayer under the tradename Desmophen).

One resin which works well for this application is an isocyanate known as Isonate 143L available from Dow Chemical Company (a mixture containing about 73% MDI) and polypropylene oxide polyol (from Bayer known as Multrinol E9109). To prolong the shelf life of the material, it is preferred to include from 0.1 to 1.0 percent by weight of benzoyl chloride or other stabilizer.

The reaction of isocyanate groups with water produces carbon dioxide. This in turn causes the polymer to foam. This foaming can cause problems with porosity. The foaming can be minimized with the addition of a silicone antifoam, a silicone surfactant, or a silicone fluid. The concentration for them can range from 0.10 to 1.00 percent.

The reactivity of the resin, once it is exposed to the water curing agent, can be controlled by proper catalyst. The catalyst should be in sufficient quantity to cause the cross-linking reaction between polyurethane prepolymer and water. However, the reactivity must not be so great that a hard film quickly forms on the resin surface preventing further water penetration into the bulk of the resin, or the cast becomes rigid before the application and the shaping is complete. The catalyst used in the urethane prepolymer can either be a tertiary amine, an organometallic compound, or a combination of both.

The reactive fluid polyisocyanate prepolymer resin is impregnated in the fabric which hardens when the resin is wetted with water. Preferably the viscosity of the reactive fluid polyisocyanate prepolymer resin ranges from 5000 centipoise to 30,000 centipoise using a Brookfield viscometer and a #4 spindle. The amount of reactive fluid polyisocyanate prepolymer resin ranges from 60 to 145 grams for a standard 3 inch (7.6 cm) by 144 inch (366 cm) piece of fabric.

ALTERNATIVE EMBODIMENTS

The orthopedic casting fabric may be modified so that the fibers used have an affinity for polyurethane. The fibers may be treated with either an aromatic urethane emulsifier or an aliphatic urethane emulsifier. These urethane emulsifiers coat the acrylic fibers so that they are more compatible with the urethane prepolymer. This increased compatibility corresponds to increased strength as shown in the table below.

STRENGTH WITH URETHANE EMULSIFIER

| Sample Number | Strength (lbs.) | Strength (kgs.) | Comment |
|---|---|---|---|
| 1 | 120 | 54 | With Bonding Agent |
| 2 | 125 | 57 | With Bonding Agent |
| 3 | 90 | 41 | Without Bonding Agent |
| 4 | 82 | 37 | Without Bonding Agent |
| 5 | 85 | 39 | Without Bonding Agent |
| 6 | 70 | 32 | Without Bonding Agent |

This system does not have to be limited to urethane. Any type of resin capable of cross-linking to form a unified mass will work provided that the limitations imposed by placement on the human body are accounted for such as heat, toxicity and fumes. The concept of having a fiber that can be mechanically or chemically connected to the resulting polymer, once polymerization has been activated, is important. It is also important to use a multi-filament yarn to create a fabric which provides sufficient surface area to accommodate the pre-polymer. A myriad of other resin system capable of polymerizing or cross-linking can be utilized.

The invented system makes the coloring of casts much simpler than has heretofore been possible. High modulus fiberglass strands will not retain color on their own. The only way to add color to high modulus fiberglass is to dye the prepolymer as taught in Polta, U.S. Pat. No. 5,052,380. Through the use of a low modulus synthetic fiber, the fabric substrate can be solution dyed, package dyed or fabric dyed, to provide casts of various colors. It is also possible to dye the yarns as they are extruded. The underlying fabric can be colored before any prepolymer is added, thus multi-color complex patterns can be provided, such as polka dot, paisley, plaid, stripes, indicia, cartoon figures, geometric patterns and combinations thereof.

EXAMPLES

Conventional polyester/cotton substrates are made from textured yarns. Fiberglass substrates are produced from monofilament fibers. When a polyester/cotton substrate is combined with a polyurethane prepolymer, it will produce a cast, but the cast is very weak and is inferior when compared to fiberglass.

However, a substrate using the new fabric technology of the present invention produces a cast that is greater in strength than a polyester/cotton cast and of equal or greater strength than a fiberglass cast. The data below illustrates this.

Procedure For Making Cast Tape Clinders

For each sample tested, a test cylinder was created using a five step method. First, immerse a roll of cast tape in a vessel of water (75° F.,+/−1° F., 24° C.). When the roll is in the water, squeeze the roll four to five times. Remove the roll from the water. Second, wrap the tape around a 2.375 (O.D.) mandrel. (Be sure to wrap some wax paper around the mandrel to prevent the cylinders from sticking to it.) Third, when wrapping the roll, place one layer on top of the preceding one until a cylinder is formed with five layers. Overlap the fifth layer no more than 1" (2.5 cm) beyond the starting point of the first wrap. Cut the rest of the roll from the cylinder. Fourth, repeat step three until all of the five wrap cylinders are made from the roll of cast tape.

Example 1

A sample cylinder was prepared according to the above procedure using a commercially available non-glass fabric substrate treated with a urethane prepolymer (In this example the Tape is a 3" Fabric Casting Tape produced by a leading manufacture). The sample cylinder was placed in an Instron (the brand name for a machine widely used in the industry to test compression strength, sold by Instron Corporation, 100TR Royall Street, Canton, Mass., 02021) and the force required to crush (defined as a deflection of the cylinder by 0.4 inch or 1 cm) the sample was recorded.

| CURRENT LOW MODULUS FIBER AND PREPOLYMER | | |
|---|---|---|
| Sample Number | Strength (lbs.) | Strength (kgs.) |
| 1 | 9.0 | 4.1 |
| 2 | 9.0 | 4.1 |
| 3 | 6.0 | 2.7 |
| 4 | 10.0 | 4.5 |
| 5 | 9.5 | 4.3 |
| 6 | 9.0 | 4.1 |

Example 2

A sample cylinder was prepared according to the above procedure using a commercially available fiberglass fabric substrate treated with a urethane prepolymer (In this example 3" Fiberglass Casting Tape produced by a leading manufacturer). The sample cylinder then was placed in an Instron and the force required to crush the sample was recorded.

| CURRENT HIGH MODULUS FIBER AND PREPOLYMER | | |
|---|---|---|
| Sample Number | Strength (lbs.) | Strength (kgs.) |
| 1 | 110 | 49.9 |
| 2 | 120 | 54.4 |
| 3 | 115 | 52.2 |
| 4 | 115 | 52.2 |
| 5 | 120 | 54.4 |
| 6 | 116 | 52.6 |
| 7 | 112 | 50.8 |
| 8 | 108 | 49.0 |
| 9 | 116 | 52.6 |
| 10 | 114 | 51.7 |

Example 3

A sample cylinder was prepared according to the above procedure using a commercially available fiberglass fabric substrate treated with a urethane prepolymer (In this example the Tape is a 3" Fiberglass Casting Tape produced by another leading manufacture). The sample cylinder was then placed in an Instron and the force required to crush the sample was recorded.

| CURRENT HIGH MODULUS FIBER AND PREPOLYMER | | |
|---|---|---|
| Sample Number | Strength (lbs.) | Strength (kgs.) |
| 1 | 95 | 43.1 |
| 2 | 100 | 45.4 |
| 3 | 100 | 45.4 |
| 4 | 90 | 40.8 |
| 5 | 96 | 43.5 |
| 6 | 94 | 42.6 |
| 7 | 80 | 36.3 |
| 8 | 87 | 39.5 |
| 9 | 86 | 39.0 |

Example 4

A sample five wrap cylinder was prepared according to the above procedure using a commercially available non-fiberglass fabric substrate treated with a urethane prepolymer (In this example the Tape is a 3" elastic fiber, low modulus casting tape produced by yet another leading manufacturer). The sample cylinder was then placed in an Instron and the force required to crush the sample was recorded.

| CURRENT LOW MODULUS FIBER AND PREPOLYMER | | |
|---|---|---|
| Sample Number | Strength (lbs.) | Strength (kgs.) |
| 1 | 40 | 18.1 |
| 2 | 40 | 18.1 |
| 3 | 40 | 18.1 |

Example 5

A sample cylinder was prepared according to the above procedure using the present invention, an optimized low modulus fabric substrate treated with a urethane prepolymer. (In this example the Tape is a Clinitex™ Medical 3" Acrylic Fabric Casting Tape). The sample cylinder was then placed in an Instron and the force required to crush the sample was recorded.

| OPTIMIZED LOW MODULUS FIBER AND PREPOLYMER | | |
|---|---|---|
| Sample Number | Strength (lbs.) | Strength (kgs.) |
| 1 | 110 | 49.9 |
| 2 | 115 | 52.2 |
| 3 | 115 | 52.2 |
| 4 | 112 | 50.8 |
| 5 | 128 | 58.1 |
| 6 | 130 | 59.0 |
| 7 | 116 | 52.6 |
| 8 | 117 | 53.1 |
| 9 | 118 | 53.5 |
| 10 | 112 | 50.8 |
| 11 | 118 | 53.5 |
| 12 | 130 | 59.0 |
| 13 | 126 | 57.2 |
| 14 | 108 | 49.0 |
| 15 | 128 | 58.1 |
| 16 | 120 | 54.4 |
| 17 | 122 | 55.3 |
| 18 | 132 | 59.9 |
| 19 | 113 | 51.3 |
| 20 | 124 | 56.2 |
| 21 | 122 | 55.3 |
| 22 | 128 | 58.1 |
| 23 | 122 | 55.3 |
| 24 | 130 | 59.0 |

The above samples of the optimized low modulus fiber system used no urethane emulsifier. The test fabric was constructed with a herringbone twill. The reason for this outstanding strength is that the acrylic substrate has more bulk than the polyester-cotton. More importantly, the acrylic yarn has more mass than the yarns used to construct the polyester/cotton. In addition, the acrylic yarn has more fibers per strand cross section of yarn than the polyester/cotton. This increase in fibers per cross section allows more prepolymer to be absorbed. As a result, a cast made from the acrylic yarn has greater strength and lamination compared to polyester/cotton.

The data below illustrates the greater lamination strength. The lamination was tested thirty minutes after water immersion.

LAMINATION COMPARISON CHART

| Samples | Fabric Type | Lamination (lbs.) | Lamination (kgs.) |
|---|---|---|---|
| 1 | Polypropylene/Lycra | 27.1 | 12.3 |
| 2 | Polyester | 35.9 | 16.3 |
| 3 | Fiberglass | 40.4 | 18.3 |
| 4 | Polyester/Spandex | 33.04 | 15.0 |
| 5 | Fiberglass | 38.1 | 17.3 |
| 6 | Fiberglass | 45.0 | 20.4 |
| 7 | Fiberglass | 51.3 | 23.3 |
| Clinitex ™ 8 | Acrylic | 62.3 | 28.3 |
| Clinitex ™ 9 | Acrylic | 73.0 | 33.1 |
| Clinitex ™ 10 | Acrylic | 71.9 | 32.6 |

Increasing the amount of polyurethane prepolymer on a polyester/cotton substrate causes some functional problems for it. The first problem is that increasing the amount of prepolymer creates a higher exotherm for this cast. This can cause discomfort to the person who is having the cast applied and may even lead to burns. Secondly, additional prepolymer added to the polyester/cotton substrate causes foaming in the cast tape. This makes it very difficult for a doctor or cast technician to mold the cast on the patient. One result is a more brittle polymer, which reduces strength. Additionally, foaming causes poor lamination to occur which ultimately decreases the strength of the cast. Finally, with the limited absorbency of the polyester-cotton substrate, excess polyurethane prepolymer may run off the substrate. This is very evident when the product is taken from the pouch in which it is stored prior to being used. A cast technician or doctor seeing prepolymer in the pouch would doubt that the product is evenly coated.

Fiberglass substrates share the very same problems with the polyester/cotton substrates when more prepolymer is added to them. Fiberglass substrates do not absorb the polyurethane prepolymer, all the polymer sits on the exterior surface. The commonality of all of this is simple. There is a narrow range of prepolymer that the polyester/cotton and fiberglass substrates can accept on its surface and still result in a functional roll of cast tape. However, the acrylic substrate has a broad range of prepolymer it can absorb to make a functional roll of cast tape. This can be attributed to the bulk of the acrylic substrate. Some slight modifications to the prepolymer can be made to optimize the setting time. The data in the table listed below illustrate that the acrylic has a broader range to absorb the prepolymer than the polyester/cotton. The comparison uses three-inch tape.

PREPOLYMER LOADING CHART

| Type of Cast Tape | Amount of Prepolymer (grams) | Amount of Prepolymer (ounces) |
|---|---|---|
| Polyester | 38–40 | 1.3–1.4 |
| Fiberglass | 60–66 | 2.1–2.3 |
| Acrylic | 90–128 | 3.2–4.5 |

It is evident that the acrylic cast tape has a broader range of amount of prepolymer that can be added to it than to fiberglass and polyester/cotton. This large range can give the user greater flexibility to determine how strong the cast tape must be. However, when the amount of prepolymer in polyester and fiberglass substrate is reduced, the strength is lowered, and in fact, the cast may not be functional. In addition, there may not be enough polyurethane prepolymer present to coat the substrate evenly.

SUMMARY OF THE ACHIEVEMENT OF THE OBJECTS OF THE INVENTION

From the foregoing, it is readily apparent that we have invented an improved composition for orthopedic casting material having strength and porosity characteristics which heretofore have been associated only with high modulus fibers, while using casting material comprising a fabric made from a low modulus fiber. We have also invented an improved method for making orthopedic casts.

One distinct advantage of this system is that the use of low modulus fibers allows production of nonwoven fabrics, woven fabrics and knitted fabrics in a variety of widths, or gives the capability of being cut a the desired width. By eliminating fiberglass, the cast becomes more radiolucent. The cast can be colored without having to place any dye in the prepolymer. Additionally the system is cost effective.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. An orthopedic casting material comprising:
   a fabric comprising:
      multi-filament acrylic yarns having a yarn count ranging from 7 to 36, each filament ranging from 6 denier to 0.5 denier; and
   a reactive fluid prepolymer resin impregnated in said fabric, said resin penetrates and surrounds and operatively fills the interstices between the filaments of said yarns, said resin hardens when said resin is activated with an activation agent.

2. The orthopedic casting material according to claim 1 wherein said yarn count ranges from 12 to 36.

3. The orthopedic casting material according to claim 2 wherein said yarn count ranges from 16 to 24.

4. The orthopedic casting material according to claim 1 wherein each filament ranges from 3 denier to 0.8 denier.

5. The orthopedic casting material according to claim 4 wherein each filament ranges from 2.0 denier to 1.0 denier.

6. The orthopedic casting material according to claim 1 wherein said yarn is 2 ply.

7. The orthopedic casting material according to claim 6 wherein said yarn count is 18.

8. The orthopedic casting material according to claim 1 wherein said yarn is multi-ply.

9. The orthopedic casting material according to claim 1 wherein said filaments have an initial modulus of elasticity of less than $3 \times 10^6$ pounds per square inch.

10. The orthopedic casting material according to claim 1 wherein said fabric is selected from the group consisting of non-woven, woven and knitted fabrics.

11. The orthopedic casting material according to claim 1 wherein said fabric is a herringbone twill.

12. The orthopedic casting material according to claim 1 wherein said yarns have an affinity for polyurethane.

13. The orthopedic casting material according to claim 1 wherein said yarns are treated with an aromatic urethane emulsifier applied to each filament of said yarns.

14. The orthopedic casting material according to claim 1 wherein said yarns are treated with an aliphatic urethane emulsifier applied to each filament of said yarns.

15. The orthopedic casting material according to claim 1 wherein said reactive fluid polyisocyanate prepolymer resin has a viscosity ranging from 5000 centipoise to 30,000 centipoise.

16. The orthopedic casting material according to claim 1 wherein said reactive fluid polyisocyanate prepolymer resin ranges from 20 to 50 grams per inch (2.5 cm) width for a roll 144 inches (366 cms) long.

17. The orthopedic casting material according to claim 1 wherein said filaments per cross section range from 100 to 500.

18. The orthopedic casting material according to claim 17 wherein said filaments per cross section range from 150 to 400.

19. The orthopedic casting material according to claim 1 wherein said reactive fluid prepolymer is a resin capable of cross-linking to form a unified mass where byproduct of heat, toxicity and fumes are within human tolerances.

20. The orthopedic casting material according to claim 1 wherein said activation agent is selected from the group consisting of water, catalyst, epoxy and mixtures thereof.

21. The orthopedic casting material according to claim 1 wherein said reactive fluid prepolymer is a polyisocyanate prepolymer which hardens when said resin is wetted in water.

22. The orthopedic casting material according to claim 1 wherein said fabric is dyed before being impregnated with said reactive fluid prepolymer resulting in a colored cast.

23. The orthopedic casting material according to claim 22 wherein said fabric is dyed with multi-colored dyes before being impregnated with said reactive fluid prepolymer, resulting in a multi-color complex pattern.

24. The orthopedic casting material according to claim 23 wherein said fabric is dyed before being impregnated with said reactive fluid prepolymer, resulting in a multi-color complex pattern selected from the group consisting of polka dots, paisley, plaid, stripes, indicia, cartoon figures, geometric patterns and combinations thereof.

25. The orthopedic casting material according to claim 1 wherein said yarn is a two ply, 18 count yarn of acrylic having from 200 to 300 1.2 denier filaments of acrylic per cross section of yarn.

26. An orthopedic casting material comprising:
 a fabric made from multi-filament acrylic yarns comprising:
  a yarn count ranging from 7 to 36;
  each filament ranging from 6 denier to 0.5 denier; and
 a reactive fluid polyisocyanate prepolymer resin impregnated in said fabric, said resin hardens when said resin is wetted with water, said resin residing on the exterior of each filament of said yarns and in the interstices between each filament of said yarns;
 wherein said orthopedic casting material has a five wrap cylinder crush strength of at least 85 pounds (39 kilograms).

27. The orthopedic casting material according to claim 26 wherein said yarn is 2 ply.

28. The orthopedic casting material according to claim 26 wherein said filaments have an initial modulus of elasticity of less than $3 \times 10^6$ pounds per square inch.

29. The orthopedic casting material according to claim 26 wherein said fabric is selected from the group consisting of non-woven, woven and knitted fabrics.

30. The orthopedic casting material according to claim 26 wherein said fabric is a herringbone twill.

31. The orthopedic casting material according to claim 26 wherein said yarns are treated with a urethane emulsifier applied to each filament of said yarns.

32. The orthopedic casting material according to claim 26 wherein filaments per cross section of yarn range from 100 to 500.

33. The orthopedic casting material according to claim 26 wherein said reactive fluid polyisocyanate prepolymer resin has a viscosity ranging from 5000 centipoise to 30,000 centipoise.

34. The orthopedic casting material according to claim 26 wherein said reactive fluid polyisocyanate prepolymer resin ranges from 20 to 50 grams per inch (2.5 cm) width for a roll 144 inches (366 cms) long.

35. An orthopedic casting material comprising:
 a fabric made from multi-filament acrylic yarns, said yarns having a yarn count ranging from 7 to 36;
 a urethane emulsifier applied to each filament; and
 a reactive fluid polyisocyanate prepolymer resin impregnated in said fabric which hardens when said resin is wetted with water, said resin residing on the exterior of each filament of said yarns and in the interstices between each filament of said yarns.

36. The orthopedic casting material according to claim 35 wherein said yarn is 2 ply.

37. The orthopedic casting material according to claim 35 wherein said filaments have an initial modulus of elasticity of less than $3 \times 10^6$ pounds per square inch.

38. The orthopedic casting material according to claim 35 wherein said fabric is selected from the group consisting of non-woven, woven and knitted fabrics.

39. The orthopedic casting material according to claim 35 wherein said urethane emulsifier is aromatic.

40. The orthopedic casting material according to claim 35 wherein said urethane emulsifier is aliphatic.

41. The orthopedic casting material according to claim 35 wherein said yarns contain from 100 to 500 filaments per cross section of yarn.

42. The orthopedic casting material according to claim 35 wherein said reactive fluid polyisocyanate prepolymer resin has a viscosity ranging from 5000 centipoise to 30,000 centipoise.

43. The orthopedic casting material according to claim 35 wherein said reactive fluid polyisocyanate prepolymer resin ranges from 20 to 50 grams per inch (2.5 cm) width for a roll 144 inches (366 cms) long.

44. An orthopedic casting material comprising:
 a fabric made from multi-filament acrylic yarns comprising:
  multi-filament yarns having a range between 100 and 500 filaments per cross section, said yarns having a count ranging from 12 to 36;
  each filament ranging from 6 denier to 0.5 denier;
 a reactive fluid polyisocyanate prepolymer resin impregnated in said fabric, said resin hardens when said resin is wetted with water, said resin residing on the exterior of each filament of said yarns and in the interstices between each filament of said yarns.

45. The orthopedic casting material according to claim 44 wherein said yarn is 2 ply.

46. The orthopedic casting material according to claim 44 wherein said filaments have an initial modulus of elasticity of less than $3 \times 10^6$ pounds per square inch.

47. The orthopedic casting material according to claim 44 wherein said fabric is selected from the group consisting of non-woven, woven and knitted fabrics.

48. The orthopedic casting material according to claim 44 wherein said fabric is a herringbone twill.

49. The orthopedic casting material according to claim 44 wherein said yarns are treated with a urethane emulsifier applied to each filament of said yarns.

50. The orthopedic casting material according to claim 44 wherein said reactive fluid polyisocyanate prepolymer resin has a viscosity ranging from 5000 centipoise to 30,000 centipoise.

51. The orthopedic casting material according to claim 44 wherein said reactive fluid polyisocyanate prepolymer resin ranges from 20 to 50 grams per inch (2.5 cm) width for a roll 144 inches (366 cms) long.

52. An orthopedic casting material comprising:
   a colored fabric made from multi-filament acrylic yarns comprising:
      a yarn count ranging from 7 to 36;
      each filament ranging from 6 denier to 0.5 denier;
      each filament being dyed while it is extruded;
   a reactive fluid polyisocyanate prepolymer resin impregnated in said fabric, said resin hardens when said resin is wetted with water, said resin residing on the exterior of each filament of said yarns and in the interstices between each filament of said yarns.

53. The orthopedic casting material according to claim 52 wherein said yarn is 2 ply.

54. The orthopedic casting material according to claim 52 wherein said filaments have an initial modulus of elasticity of less than $3 \times 10^6$ pounds per square inch.

55. The orthopedic casting material according to claim 52 wherein said fabric is selected from the group consisting of non-woven, woven and knitted fabrics.

56. The orthopedic casting material according to claim 52 wherein said fabric is a herringbone twill.

57. The orthopedic casting material according to claim 52 wherein said yarns are treated with a urethane emulsifier applied to each filament of said yarns.

58. The orthopedic casting material according to claim 52 wherein said yarns contain from 100 to 500 filaments per cross section of yarn.

59. The orthopedic casting material according to claim 52 wherein said reactive fluid polyisocyanate prepolymer resin has a viscosity ranging from 5000 centipoise to 30,000 centipoise.

60. The orthopedic casting material according to claim 52 wherein said reactive fluid polyisocyanate prepolymer resin ranges from 20 to 50 grams per inch (2.5 cm) width for a roll 144 inches (366 cms) long.

61. An orthopedic cast which comprises:
   a fabric made from multi-filament acrylic yarns, said multi-filament acrylic yarns having a yarn count ranging from 7 to 36, where each filament ranges from 6 denier to 0.5 denier; and
   a reactive prepolymer resinous material which coats and impregnates the fabric, said resinous material residing on the exterior of each filament of said yarns and in the interstices between each filament of said yarns;
   wherein said fabric is initiated to start polymerization and said fabric is wrapped about itself to form a coil which cures into a cast.

62. The orthopedic cast according to claim 61 wherein said reactive prepolymer resinous material is a polyisocyanate prepolymer which hardens when said resin is wetted in water.

63. The orthopedic cast according to claim 62 wherein said reactive prepolymer resinous material is initiated by immersing the impregnated fabric into a wetting solution to wet the resin.

64. The orthopedic casting material according to claim 62 wherein said reactive fluid polyisocyanate prepolymer resin has a viscosity ranging from 5000 centipoise to 30,000 centipoise.

65. The orthopedic cast according to claim 62 wherein said reactive fluid polyisocyanate prepolymer resin ranges from 20 to 50 grams per inch (2.5 cm) width for a roll 144 inches (366 cms) long.

66. The orthopedic cast according to claim 61 wherein said reactive prepolymer is a resin capable of cross-linking to form a unified mass, and wherein byproducts of heat, toxicity and fumes are within human tolerances.

67. The orthopedic cast according to claim 61 wherein initiation comes from an activation agent selected from the group consisting of water, catalyst, epoxy and mixtures thereof.

68. The orthopedic cast according to claim 61 wherein said yarns are 2 ply.

69. The orthopedic cast according to claim 61 wherein said filaments have an initial modulus of elasticity of less than $3 \times 10^6$ pounds per square inch.

70. The orthopedic cast according to claim 61 wherein said fabric is selected from the group consisting of non-woven, woven and knitted fabrics.

71. The orthopedic cast according to claim 61 wherein said yarns are treated with a urethane emulsifier applied to each filament of said yarns.

72. The orthopedic cast according to claim 61 wherein yarns range from 100 to 500 filaments per cross section of yarn.

73. The orthopedic cast according to claim 61 wherein said fabric is a herringbone twill.

74. The orthopedic cast according to claim 61 wherein said fabric is dyed before being impregnated with said reactive prepolymer, resulting in a colored cast.

75. The orthopedic cast according to claim 74 wherein said fabric is dyed with multi-colored dyes before being impregnated with said reactive prepolymer, resulting in a multicolor complex pattern.

76. The orthopedic cast according to claim 75 wherein said fabric is dyed before being impregnated with said reactive prepolymer, resulting in a multi-color complex pattern selected from the group consisting of polka dots, paisley, plaid, stripes, indicia, cartoon figures, geometric patterns and combinations thereof.

77. The orthopedic cast according to claim 61 wherein said yarn count ranges from 12 to 36.

78. The orthopedic cast according to claim 61 wherein each filament ranges from 3 denier to 0.8 denier.

\* \* \* \* \*